United States Patent [19]

House

[11] 4,424,057
[45] Jan. 3, 1984

[54] WET-DRY SYRINGE

[76] Inventor: Hugh A. House, 159 Lincoln Rd., Wenonah, N.J. 08090

[21] Appl. No.: 364,496

[22] Filed: Apr. 1, 1982

[51] Int. Cl.³ .............................................. A61M 5/22
[52] U.S. Cl. .................................................. 604/88
[58] Field of Search ..................... 604/88, 201, 82, 87, 604/200, 306, 3, 205

[56] References Cited

U.S. PATENT DOCUMENTS

| | | | |
|---|---|---|---|
| 3,563,373 | 2/1971 | Paulson | 604/88 |
| 3,785,379 | 1/1974 | Cohen | 604/88 |
| 3,884,229 | 5/1975 | Raines et al. | 604/205 |
| 3,895,633 | 7/1975 | Bartner et al. | 604/201 |
| 4,031,892 | 6/1977 | Hurschman | 604/88 |

*Primary Examiner*—John D. Yasko
*Attorney, Agent, or Firm*—Martin Sachs

[57] ABSTRACT

A wet-dry syringe for combining and mixing a liquid and a solid medicament or at least two dissimilar liquid medicaments prior to the application thereof to a patient includes a first vial having liquid or solid medicament disposed between a pair of identical vial seals. A second vial functions as a piston rod and includes a pair of end seals with a liquid medicament disposed therein. One of the second vial seals includes a hollow piercing needle which when utilized to pierce one end seal of the first vial causes the medicament therein to flow into the first vial thereby mixing the medicaments prior to application to a patient by means of a needle piercing assembly which pierces the second of the first vial seals and the patient to which the mixed medicaments are to be infused. The second vial functions as a piston rod and aides in the discharge of the medicaments.

9 Claims, 16 Drawing Figures

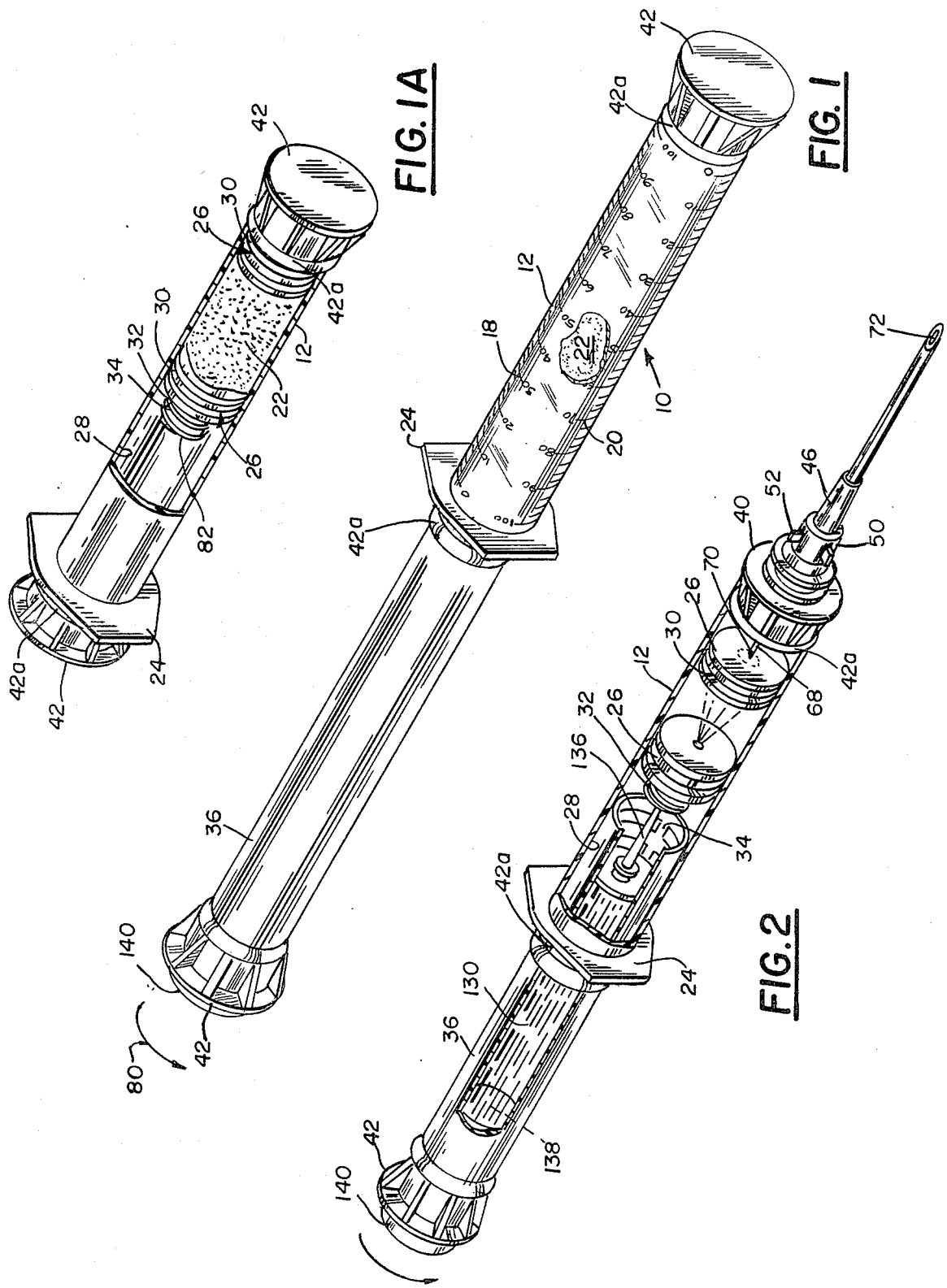

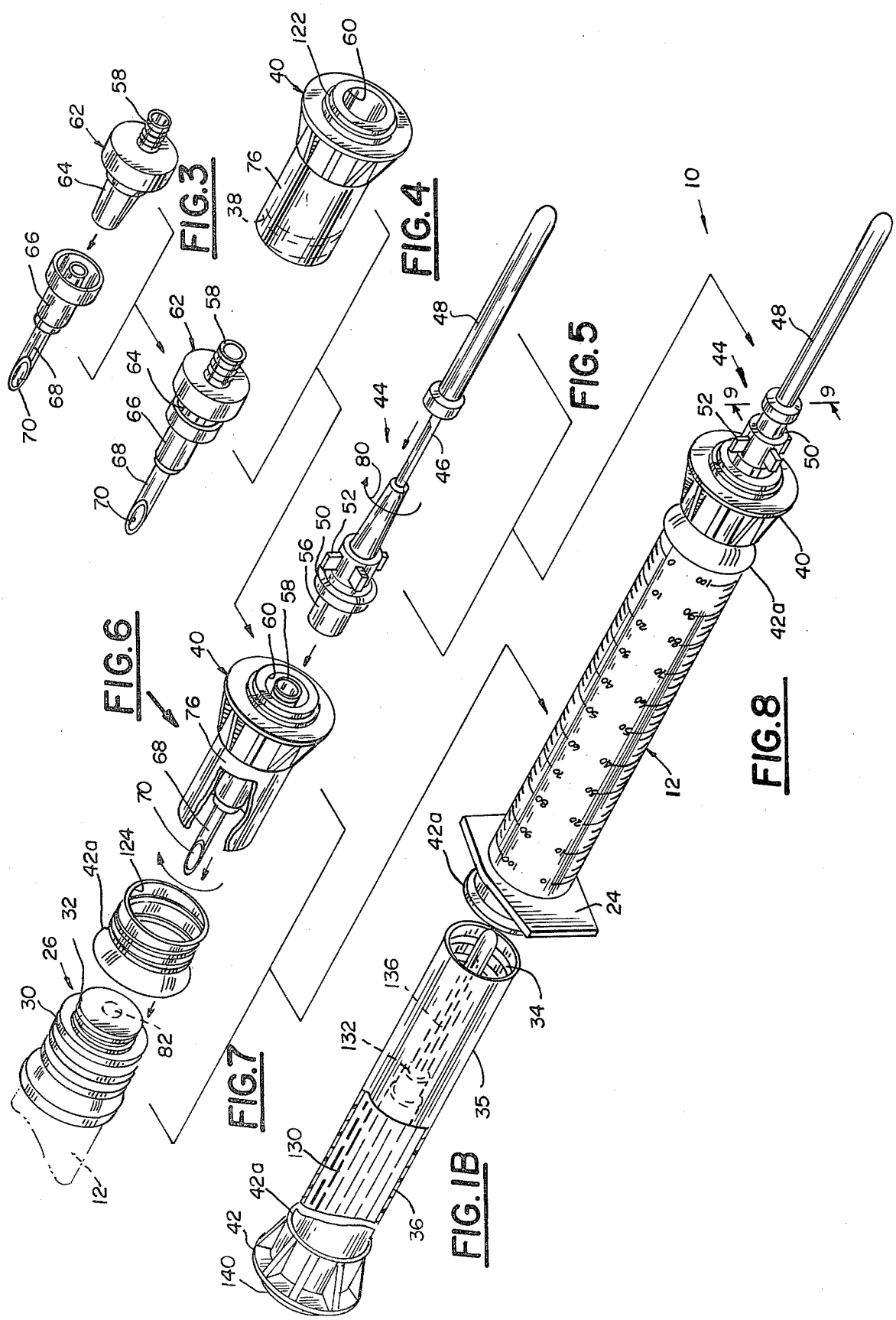

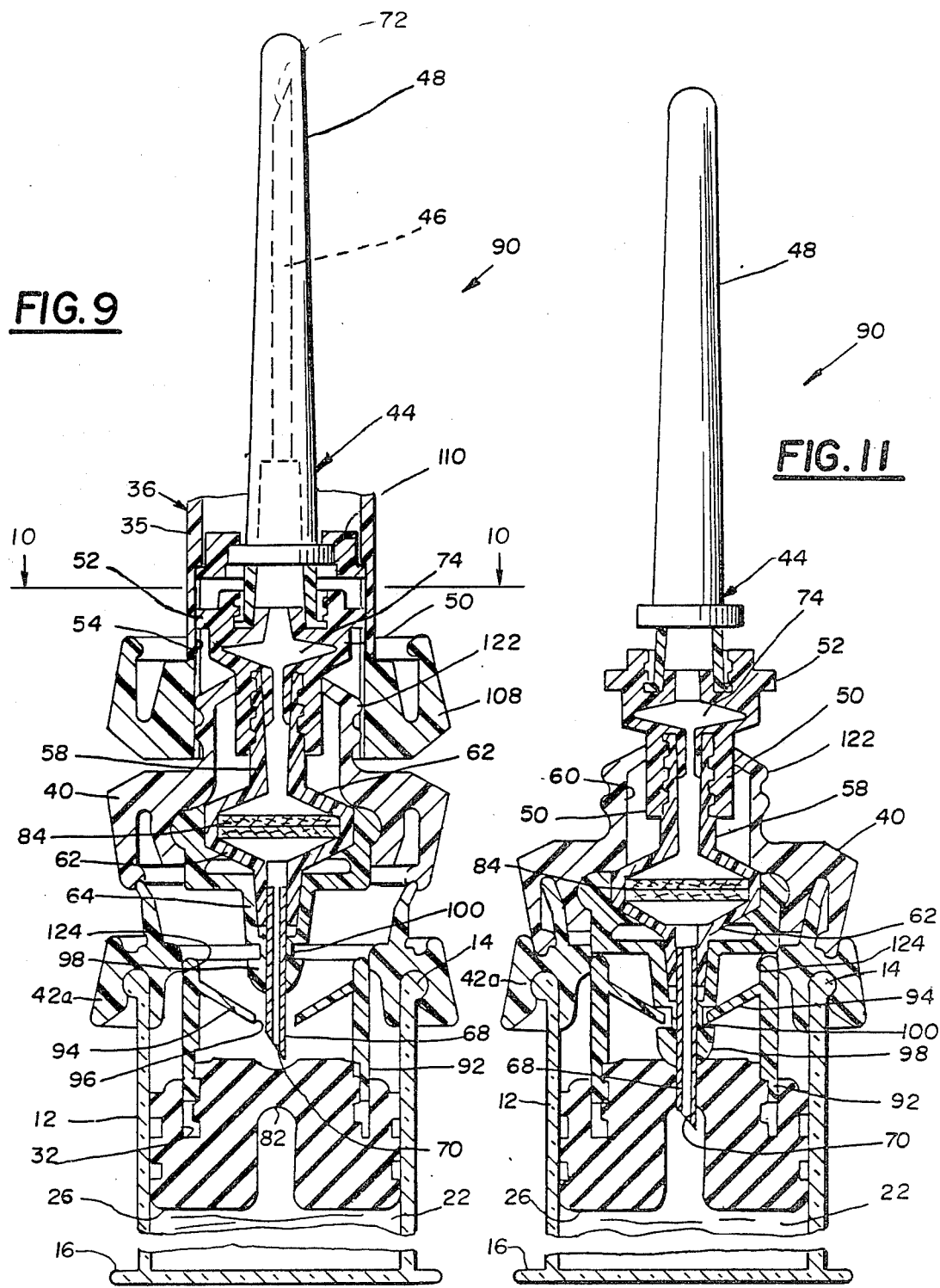

WET-DRY SYRINGE

BACKGROUND OF THE INVENTION

1. Field of the Invention

The present invention relates to hypodermic syringes, and in particular, to a universal syringe which may be utilized for combining and mixing a solid and a liquid medicament or at least two dissimilar liquid medicaments prior to the application thereof to a patient.

2. Discussion of the Relevant Art

The art abounds with designs for hypodermic syringes and needle assemblies, particularly of the type wherein the medicament retaining vial is inserted into one end of the syringe barrel and the transfer needle assembly. The syringe plunger urges the vial against the needle piercing portion of the transfer needle and permits the medicament to flow from the vial to the needle piercing assembly and transfer needle. This type of arrangement is disclosed in U.S. Pat. No. 3,884,229 issued to Raines, et al. on May 20, 1975. The medicament holding vial disclosed therein has a plunger proof seal on one end thereof and a pierceable seal on the other end and is positioned so that the piercing needle is accurately aligned to the center of the seal while the other end is provided with a plunger with which the user provides the necessary pressure to force the vial against the piercing needle, thereby permitting the medicament, once the seal in the vial is pierced, to communicate through the needle piercing aperture to the transfer needle and thus, into the patient.

Another syringe utilizing a pre-filled vial which has one end of the vial sealed by means of a rubber diaphragm and the other end thereof sealed by a stopper is disclosed in U.S. Pat. No. 3,989,044 issued to Meierhoefer on Nov. 2, 1976. A needle hub assembly associated with the vial is used to pierce the stopper, thereby permitting the medicament contained within the vial to communicate with the transfer needle, and thus, into the patient.

Although there has been a need for many years to mix either a liquid medicament with a solid medicament or two different medicaments just prior to use, the device to accomplish this does not appear to be available. In order to extend the life of the medicament once sealed in a vial, it may be advantageous to use the medicament in a crystalline configuration and then add to it, just prior to use, the desired liquid solvent to form a solution which may have a limited shelf life. Thus, during storage the crystalline medicament, stored under vacuum conditions within the vial, may have extended or possible infinite life. The present invention is directed to a universal syringe configuration consisting of two separate vials which may be combined to provide the medicament to a patient without being concerned with the shelf life of the mixed medicament in the vial.

The shortcomings of the prior art devices are overcome by the instant invention, since the instant disclosure utilizes a vial which is identical on both ends, may be used interchangeably, and has stored therein either a stable medicament in liquid or crystalline form which has been placed in the vial under a vacuum. The vial may be assembled with its cooperating plunger having a hollow configuration and including therein the required liquid so that when combined with the medicament in the first vial will provide a solution just prior to application to a patient, thereby removing the concern of the medicament losing its strength because of extended shelf time.

Therefore, it is an object of the present invention to provide a universal syringe and associated plunger arrangement which would provide for the mixing of two medicaments just prior to use.

It is another object of the present invention to provide a wet-dry syringe which may be rapidly assembled in an emergency situation.

It is yet another object of the present invention to provide a wet-dry syringe wherein the piston rod assembly is adapted to be received into either end of the vial in which the solid medicament has been stored.

It is yet another object of the present invention to provide a wet-dry syringe wherein the medicament in the vial assembly is stored under vacuum conditions and the medicament in the plunger assembly may be maintained in a sterilized condition until use.

It is still yet a further object of the present invention to provide a wet-dry syringe whereby a liquid medicament retained within the plunger assembly vial may be sealed and maintained under sterile conditions until ready for use.

A further object of the present invention is to provide a wet-dry syringe wherein a piercing needle is part of the piston assembly and is maintained out of contact with the medicament stored therein.

A further object of the present invention is to provide a wet-dry syringe wherein the storage vial is adapted to receive a micropore filter assembly capable of puncturing the vial seal with use and also adapted to receive a needle for insertion into a patient.

The foregoing and other objects and advantages will appear from the description to follow. In the description reference is made to the accompanying drawing which forms a part hereof, and in which is shown by way of illustration a specific embodiment in which the invention may be practiced. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

SUMMARY OF THE INVENTION

A wet-dry syringe, according to the principles of the present invention, for combining and mixing a liquid and a solid medicament or at least two dissimilar liquid medicaments prior to the application thereof to a patient comprises, in combination, an elongated cylindrically-shaped vial having outwardly extending lip portions proximate each end thereof and a pair of identical vial seals disposed within the cylinder vial. The vial seals are in intimate frictional contact with the internal walls of the vial and slidable therealong. The vial seals are also adapted to retain a first liquid or solid medicament therebetween. A cap is adapted to be received on each end of the vial to maintain its sterility. An elongated cylindrically-shaped piston rod is hollow and includes, a first piston rod seal disposed proximate one end thereof. The first piston rod seal is in intimate frictional contact with the internal walls of the piston rod and slidable therealong. A second piston rod seal is disposed proximate the other end of the piston rod in a fixed position. The first and second piston rod seals are adapted to retain a second liquid medicament therebetween. A hollow needle is disposed proximate the second piston rod seal. The piston rod is adapted to be received into the vial for contact with one of the pair of vial seals and when urged into contact with the vial seal causes the hollow needle to provide a fluid flow path for communication of the second liquid medicament disposed within the piston rod to flow and mix with the solid medicament or the liquid medicament disposed within the vial when urged away therefrom. A second needle has one end adapted to be inserted into a patient and the other end thereof adapted to pierce the other of the pair of vial seals and communicates with the mixed medicaments disposed within the vial. The piston rod causes the mixed medicaments to be discharged through the second needle when urged in the direction thereof.

The method of combining and mixing a liquid and a solid medicament or at least two dissimilar medicaments prior to the application thereof to a patient, according to the principles of the present invention, comprises the steps of: providing a vial having identical end seals with a solid or a liquid disposed between the seals by a vacuum process; providing a hollow piston rod having a liquid medicament disposed therein between a fixed and a movable end seal; providing a hollow piercing means proximate the fixed piston rod seal; engaging one of the vial seals with the piston rod with the piercing means disposed therebetween; applying pressure between the piston rod and the vial for the piercing means to puncture one of the vial seals; drawing the piston rod away from the vial and moving the vial seal proximate one end of the vial, the hollow piercing means providing a fluid flow path between the vial medicament and the piston rod medicament, the piston rod medicament entering the vial because of the pressure differential generated therebetween; connecting a needle assembly having a seal piercing device on one end and a patient piercing device on the other end of the vial; puncturing the remaining vial seal with the second needle assembly; and applying pressure to the piston rod in the direction of the vial to cause the combined medicaments to leave the needle assembly means into said patient.

BRIEF DESCRIPTION OF THE DRAWING

In order that the invention be made more fully understood, it will now be described, by way of example, with reference to the accompanying drawing in which:

FIG. 1 is a perspective view of a solid medicament vial connected with a piston rod vial, according to the principles of the present invention;

FIG. 1A is a perspective view, partially broken away, of a hollow multi-dose vial containing a solid medicament therein with protective end caps thereon to maintain its sterility;

FIG. 1B is a perspective view, partially broken away, of a second hollow vial including a transfer needle or a piercing needle;

FIG. 2 is a perspective view of a fully assembled syringe (including the medicament vial and piston rod vial) partially broken away;

FIG. 3 is an exploded view in perspective showing the relative position of a piercing needle and a micropore filter;

FIG. 4 is an exploded view in perspective showing a piercing needle and a filter assembly with a multi-dose vial adapter in position to receive the opposite end of a micropore filter;

FIG. 5 is an exploded view in perspective of a patient or transfer needle and needle cover in position to be received by a hollow piston rod on one end thereof;

FIG. 6 is a perspective view of the piercing needle and filter assembly with the multi-dose vial adapter in position to receive the patient needle therein on one end and in position to be received by a piston seal on the other end;

FIG. 7 is an exploded perspective view of a syringe including a medicament vial, multi-dose vial adapter, needle piercing and filter assembly, seal adapter, and piston seal together with a patient needle adapter, patient needle, needle cover and a portion of a hollow piston rod having a liquid medicament therein;

FIG. 8 is a perspective view of a syringe, showing a piston rod and a piston piercing needle with a liquid medicament retained therein about to be connected to a cooperating multi-dose vial, which may retain a solid or liquid medicament therein and contains the patient needle adapter, patient needle, and needle cover at the other end thereof;

FIG. 9 is a partial cross-sectional view in elevation of one embodiment of a fully assembled syringe at the patient needle end just prior to a piercing needle penetrating a piston seal for withdrawal of the liquid mixture medicament;

FIG. 11 is a partial cross-sectional view in elevation of the embodiment shown in FIG. 10 with the piercing needle penetrating the vial seal in position for withdrawal of the mixed liquid medicament;

DESCRIPTION OF THE PREFERRED EMBODIMENTS

Figure 13:
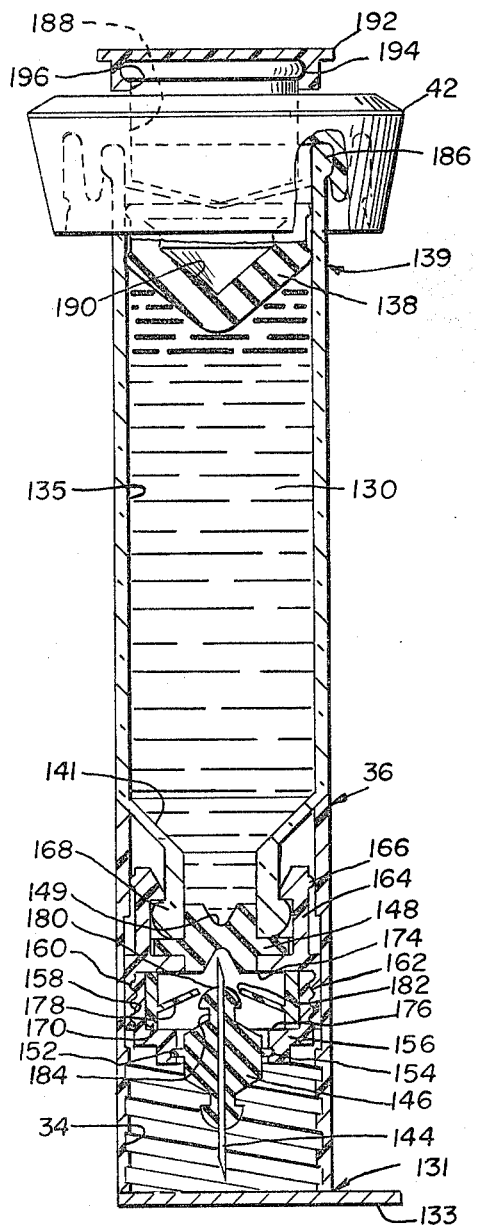
FIG. 13 is a cross-sectional view of a hollow piston rod having liquid medicament therein with a movable piston seal at one end and a fixed seal at the other end with a piercing adaptor prior to activation.

Referring now to the figures, and in particular to FIGS. 1–8, there is shown a perspective view of a wet-dry syringe 10 which includes an elongated cylindrically-shaped multi-dose vial 12, preferably made of glass, and having outwardly extending protrusions or lip portions 14 and 16 provided at the distal ends thereof (see FIGS. 9 and 11). The surface of the vial 12 is provided with indicia 18 and 20 in the form of scale graduations starting a zero at one end and reaching one hundred at the opposite end. Indicia is also provided theron starting at one hundred at the same end and reducing to zero at the opposite end. The function of the indicia provided on the vial 12 will become obvious hereinafter and is an indication of the amount of medicament 22 remaining in the vial. Preferably, the medicament 22 in the vial 12 is of a solid material or dry ingredients e.g. crystalline, powder etc. obtained by an aseptic filling in a freeze drying process. A slidable finger rest 24 encompasses the surface of the vial 12 and may be removed from one end thereof to the other, being restrained by the extending lip portions of 42a at the convenience of the individual utilizing it.

An identical pair of vial seals 26 (see FIG. 2) are disposed within the vial 12 and are in intimate frictional contact with the inner wall 28 of the vial 12 in order to contain the medicament 22, which may be in liquid or solid form, therebetween. The circumference of the vial seal 26 is provided with a plurality of ridges 30 which permit the vial seal 26 to move freely along the inner wall 28 of the vial by preventing the liquid or solid medicament from leaking therearound (see FIG. 1A). In the embodiment disclosed in FIG. 10, the vial seals 26 are provided with a threaded channel 32 circumferentially disposed proximate to the periphery of the vial seal 26. The threaded grooves are adapted to receive and cooperate with a mating thread 34 provided on the piston rod 36 (see FIG. 2) in addition to the mating thread 38 provided on the vial-adaptor 40 (see FIG. 4) as will be explained hereinafter. Thus, the vial 12 may receive the piston rod 36 on either end and is also capable of receiving the vial adaptor 40 on either end. Since each of them are capable of being received into either of the threaded channels 32 provided in the vial seal 26, they permit an individual to assemble the universal wet-dry syringe in a more rapid-like manner than possible before.

A pair of end caps or seals 42 and 42a are provided on each end of the vial 12 in order to maintain sterility of the contents thereof.

A needle assembly 44 includes a patient or transfer needle 46 and a needle cover 48. The transfer needle 46 includes a shoulder portion 50 which is provided with a plurality of outwardly extending protrusions 52 adapted to cooperate with and extend into grooves 54 provided in a hollow piston rod, not shown herein, but disclosed in patent application Ser. No. 281,842, filed on July 9, 1981. The other end of the needle assembly 44 proximate the shoulder portion 50 is provided with a conically shaped internally threaded portion 56 which is adapted to be received by an externally threaded mating protion 58 provided on the vial adapter 40 (see FIGS. 7 and 9). The portion 58 extends from the opening 60 and is one end of a micropore filter 62 disposed on the vial adapter. The other end of the micropore filter 62 is provided with a conically shaped protruding portion 64 having a shoulder 66, a piercing needle 68 cooperating therewith and removably affixed thereon in a conventional manner, as shown in FIGS. 3, 4 and 9. The piercing needle 68 is provided with an aperture 70 permitting communication therethrough into the micropore filter 62 and through the vial adaptor 40 to the aperture 72 provided in the patient or transfer needle 46. A chamber 74 (see FIG. 9) is provided between the micropore filter 62 and the patient transfer needle and the shoulder portion 50 of the transfer needle 46 in order to permit the user of the syringe to see that the transfer needle 46 has entered a vein or artery of the patient by permitting blood that has entered the chamber to be visible to the user of the syringe. Thus, the syringe user is assured of application of the medicament in the syringe directly into the patient's vein or artery.

Portion 76 of the vial adaptor 40 extends outwardly at the opposite end from the threaded portion 58 of the filter 62 and is adapted to completely encompass the filter therein and extend beyond the opposite end of the filter with internally provided threads 38 disposed therein to cooperate with and engage the threaded channel 32 provided in the vial seal 26 and as the threads 32 and 38 engage and cooperate when the needle assembly 44 is rotated in the direction of arrow 80 (see FIG. 5) the piercing needle 68 pierces the narrow portion 82 provided in the vial seal 26, thereby permitting the mixed medicaments occuring in the vial 12 to communicate with the patient, not shown, via aperture 72 provided in the patient transfer needle.

FIG. 2 shows the vial 12 with the needle assembly 44 in position on the vial and with the cover 48 of the patient or transfer needle 46 exposed. Finger rest 24 has been moved into position for use and the piston rod 36 which has a liquid medicament 130 disposed therein is about to be inserted into a vial seal 26 for use as a completed syringe. The actual assembly procedures, including mixing of the liquid medicament in the piston rod 36 and the medicament in the vial 12 will be outlined hereafter in conjunction with FIGS. 2 and 8 which show the steps in assembling the completed syringe and the means for mixing the medicaments disposed in the piston rod and the multi-dose vial 12.

FIG. 9 is an alternate embodiment 90 of the wet-dry syringe described in FIGS. 1 through 8, and like components have been given like numerical designations for clarity and will be maintained throughout the remaining figures. The vial 12 includes a pair of vial seals 26, preferably fabricated of rubber (only one being shown). The seal 26 is provided with a threaded channel 32 which is adapted to receive therein the extending portion 92 of the vial adapter 40. The extended portion 92 is provided with the plurality of inwardly extending portions 94, preferably three, which has a consentrically disposed opening 96 adapted to receive a hemispherically-shaped shoulder portion 98 therein. When the hemispherically-shaped portion 98 is forced into the opening 96 the inwardly extending portions 94 are retained in a channel 100 which extends circumferentially just behind the shoulder portion 98, thereby retaining the shoulder in a relatively fixed position which may only be removed by exerting a relatively large force therebetween. A piercing needle 68 is centrally disposed in the shoulder portion 98 in a conventional manner. Holding the vial in one hand and applying pressure to the piston rod 36 will cause the shoulder portion 98 to enter aperture 96, thereby permitting the piercing needle 68 to puncture the narrow portion 82 of the seal 26 providing communication with the solid or liquid medicament 22 disposed within the vial 12 between seals 26. At the same time that the piercing needle 68 punctures the seal 26, vial adapter 40 is caused to engage the extending lip portion 42A further adding to the security or retention of the piercing needle in position. The vial adapter 40 has inserted therein the micropore filter 62 as described hereinbefore with regard to FIGS. 4, 5, and 6.

Figure 10:
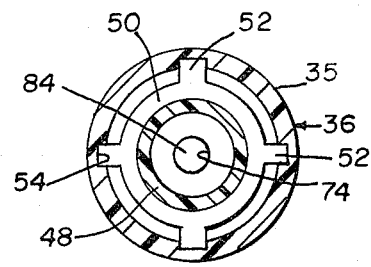
FIG. 10 is a view taken along the line 10—10 of FIG. 9.

FIG. 10 is a view taken along the line 10—10 of FIG. 9 and more clearly shows the grooves 54 provided in the internal wall of the lower portion 35 of the hollow piston rod 36 cooperating with the protrusions provided on the shoulder portion 50 of the transfer needle. The micropore filter elements 84 may be seen to close off the aperture 72 of the transfer needle 46 and prevent foreign matter from entering into the aperture 70 provided in the piercing needle 68.

FIG. 11 is a cross-sectional view which shows the position of the components after the piercing needle 68 has passed the seal 26. A piston rod, of the type disclosed in U.S. Ser. No. 281,842 may be utilized to cover the needle cover 48 and, as shown in FIG. 11, has already been removed. Needle cover 48 functions to protect the transfer needle 46.

Figure 12:
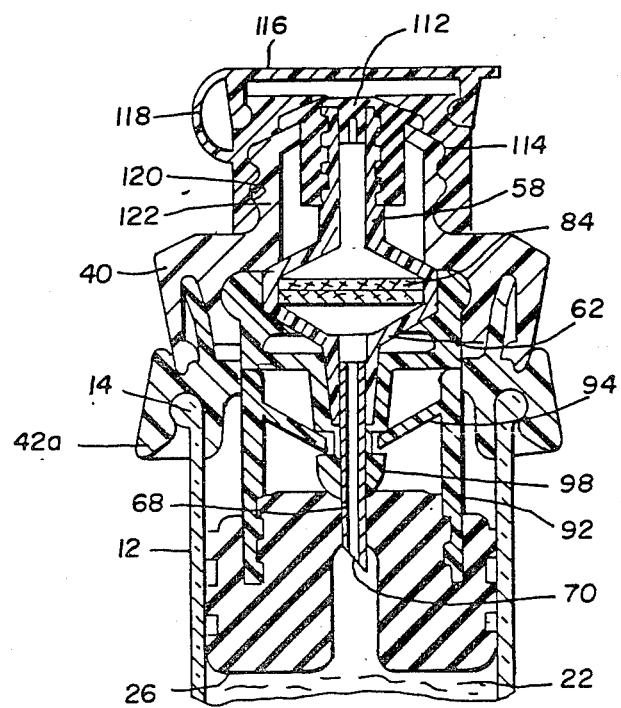
FIG. 12 is an enlarged partial cross-sectional view of the embodiment shown in FIG. 11 with the patient needle removed and replaced by a cap over the insert and micropore filter assembly in order to maintain sterility of the medicament vial.

FIG. 12 is an enlarged partial cross-sectional view of the embodiment described in conjunction with FIG. 9 with the patient or transfer needle 46 removed from the vial adapter. An adapter plug 112 may be inserted into the opening 60 left remaining by the removal of the transfer needle exposed to the portion 58 of the micropore filter 62. By providing a sealing cap 114 with a pop-off cover, the seal integrity of the system may be maintained. Cover 116 may include a living hinge 118 attaching the cover to the sealing cap so that it may be repeatedly re-used. Thus a unitary sealing cap and cover arrangment may include a micropore filter and provide communication into the medicament in the vial and yet be maintained in a sealed sterile relationship. The adapter plug 112 is, preferably, made of a rubber material which may be readily threaded on the threaded portion 58 of the micropore filter 62 and is readily deformed when the sealing cap 114 is threaded onto the threads 120 on the outwardly extending portion 122 of the vial adapter 40. As shown, the sealing cap 114 may be used on either of the disclosed embodiments.

An enlarged cross-sectional view of the piston rod 36 is shown in FIG. 13. The piston rod 36 is provided with mating threads 34 as explained earlier which are adapted to be received by the threaded channel 32 provided on the vial seals 26 and is normally disposed on the opposite end of vial 12 from the needle assembly 44. The end 131 of the piston rod 36 is provided with a tip seal 133, of the conventional type, such as Dupont's Tyvek, a material commonly staked over the end of a device to maintain sterility following sterilization of the device in a conventional manner. Disposed within the piston rod 36 is a liquid medicament 130 which is contained therein between a piston rod seal 138 disposed at the opposite end 139 and a seal 148. Seal 138 is adapted to be movable along the inner wall 135 of the piston rod 36. An inwardly extending portion 141, disposed proximate end 131, is adapted to retain the seal 148, preferably of rubber, which is maintained in a fixed position and is provided with a narrow portion 149 which is adapted to receive and be punctured by a hollow transfer needle 144 centrally disposed in a needle holder 146 which is provided with outwardly extending protrusions 152 which is adapted to cooperate with and be retained in grooves 154 provided in a needle housing 156.

Housing 156 is provided with external threads 158 which threadedly engages cooperating threads 160 provided in an extending portion 162 of a needle mounting 164. Needle mounting 164 is provided with an overhanging lip portion 166 which cooperates with a lip portion provided on the inwardly extending portion 141 of the hollow piston rod 36. By threading the needle housing 156 on to the needle mounting 164, a locking or retaining device 170 having a circumferentially disposed portion 172 fixed in position between a horizontal shoulder 174 provided on the needle mounting and an inwardly extending shoulder 176 provided on the needle housing. An inwardly extending finger 178 provided on the retaining device 170 captures the hemispherically-shaped portion of the needle holder when it extends through a centrally disposed aperture 182 provided by the fingers 178 and further helps to retain the needle holder 146 in position by the subject finger 178 entering a circumferentially disposed groove 184 provided just below the hemispherically-shaped portion 180 on the needle holder 146.

Thus, the needle holder 146 may be maintained in position without having the transfer needle 144 pierce the narrow portion 149 of the seal 148 until pressure is exerted on the needle holder 146 just prior to use. When puncturing of the seal 148 will occur simultaneously with the puncturing of seal 26.

As explained earlier, the opposite end of piston rod 36 may be provided with a cap or seal 42 which is retained on the piston rod by means of a lip portion 186 provided on the end of the piston rod and may be in the type similar to lip portions 14 and 16 discribed earlier. The cap 42 may be provided with an aperture 188 which provides clearance for a solid piston rod, not shown, adapted to be received in the shaped receptacle 190 provided in the piston rod seal 138 if it should become necessary to provide additional pressure to the piston in order to cause the liquid medicament 130 disposed within the piston rod 136 to be discharged through the hollow transfer needle 144. A cover 192 may be utilized to cover the aperture 188 of cap 42 and may be removed or retained by means of a protrusion 194 and cooperating groove 196 provided on the cover 192.

Figure 14:
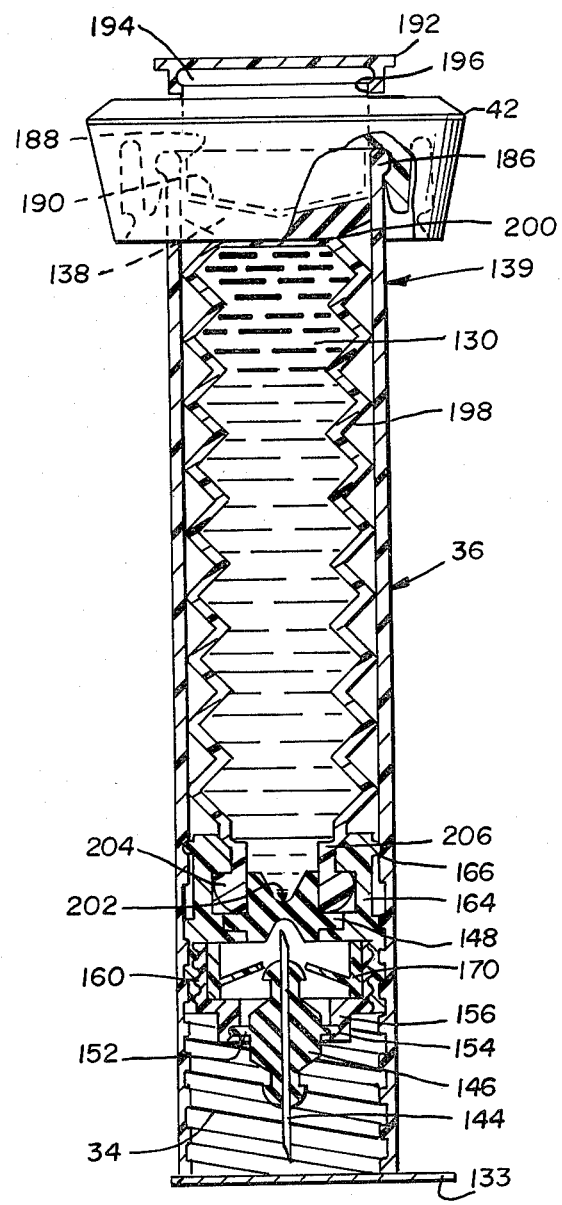
FIG. 14 is a cross-sectional view of an alternate embodiment of a piston rod showing a resilient bellows disposed within a hollow piston rod having a fixed seal with a piercing adapter disposed proximate thereto prior to activation.

The embodiment disclosed in FIG. 14 is similar to that disclosed in FIG. 13 and is therefore numbered in the same manner where the parts are identical. FIG. 14 includes the use of a membrane 198 which contains the liquid medicament therein. The membrane 198 is resilient and collapses when the medicament is drawn therefrom. The upper end 200 is sealed and maintains the medicament therein while the lower end is provided with a seal arrangement 202 which includes a seal 148 adapted to be punctured by a hollow transfer needle and a needle mounting 164 as in the embodiment disclosed in FIG. 13. However, a seal capturing device 204 which includes an extending portion 206 receives the membrane 198 thereon and is held in position in a conventional manner thus providing a replaceable independent assembly which includes the membrane 198 and a seal capturing device and a seal which may be installed into any hollow piston rod 36 as desired.

In operation, the wet-dry syringe may be used to combine either two liquid medicaments or a solid medicament disposed in the vial portion and a liquid medicament disposed in the hollow piston rod portion of the syringe. This is ideally suitable where the medicaments individually would have an infinite shelf life while the combination would have a limited shelf life thus, the mixture occurs just prior to use of the combined medicaments. The vial which preferably includes a solid medicament has identical end seals and is provided with end caps and a finger rest 24 disposed thereon which may be moved to either end and retained by the lip portions of 42a provided thereon. Since the vial is assembled with the medicament under vacuum conditions, when placed at atmospheric pressure the pistons will be drawn together compressing the solid medicament to a minimal volume. When the liquid medicament is mixed therewith the piston seal will move towards either ends as the volume increases. Caps 42 are placed on both ends to maintain the sterility of the surfaces of the vial seals. A second hollow vial functions as a piston rod 36 and may be of a type disclosed in FIGS. 1B or 13 and 14. The piston rod includes a transfer needle 136 or a piercing or transfer needle 68 as described hereinbefore. The means utilized to transfer the liquid from the piston rod 36 to the vial 12 may be accomplished with an number of cooperating configurations two of which have been disclosed herein. When the piercing means on the piston rod is urged to contact the vial seal, after removal of the cap 42, the vacuum in the vial 12 will draw the liquid medicament 130 into the vial 12 causing the solid or liquid medicaments to co-mingle. With small amounts of agitation of the vial 12 complete mixing will be accomplished. If it is necessary to assert additional pressure to insure that the medicament 130 will enter the vial 12 through the transfer needle a solid piston rod may be used to engage the movable piston seal 138 provided in the piston rod 36. Once the medicament has been mixed the needle assembly 44 may be affixed to the other end of the vial 12 in a similar manner causing the piercing needle 68 to puncture the other vial seal 26 thereby providing a continuous fluid flow path for the mixed medicaments to enter a patient. The use of a micropore filter 62 may be utilized if desired.

Hereinbefore has been disclosed a wet-dry syringe which essentially is provided in three separate assemblies permitting two medicaments to be stored independently one in a hollow piston rod, the other in a vial and means for readily mixing the two just prior to use. A needle assembly may be affixed to the vial in the same manner as the piston rod is affixed at the opposite end thereof thus making assembly and mixing of the medicaments convenient and rapid.

It will be understood that various changes in the details, materials, arrangements of parts and operating conditions which have been herein described and illustrated in order to explain the nature of the invention may be made by those skilled in the art within the principles and scope of the instant invention.

Having thus set forth the nature of the invention, what is claimed is:

1. A wet-dry syringe for combining and mixing a liquid and a solid medicament or at least two dissimilar liquid medicaments prior to the application thereof to a patient comprises, in combination:
    (a) an enlongated cylindrically-shaped vial having outwardly extending lip portions proximate each end thereof and a pair of identical vial seals disposed within said cylinder, said vial seals being in intimate frictional contact with the internal walls of said vial and slidable therealong, said vial seals being adapted to retain a first liquid or said solid medicament therebetween;
    (b) cap means adapted to be received on each end of said vial to maintain its sterility;
    (c) elongated cylindrically-shaped piston rod means; said piston rod means being hollow and including;
        (i) a first piston rod seal disposed proximate one end thereof, said first piston rod seal being in intimate frictional contact with the internal walls of said piston rod means and slidable therealong;
        (ii) a second piston rod seal being disposed proximate the other end of said piston rod means in a fixed position, said first and said second piston rod seals being adapted to retain a second liquid medicament therebetween;
        (iii) hollow needle means disposed proximate said second piston rod seal, said piston rod means being adapted to be received into said vial for contact with one of said pair of vial seals and when urged into contact with said vial seal causing said hollow needle means to provide a fluid flow path for communication of said second liquid medicament with said solid medicament or said liquid medicament disposed within said vial; and
    (d) second needle means having one end adapted to be inserted into a patient and the other end thereof adapted to pierce the other of said pair of vial seals and communicate with said mixed medicaments disposed within said vial, said piston rod means causing said mixed medicaments to be discharged through said second needle means when urged in the direction thereof.

2. A wet-dry syringe according to claim 1 wherein said cap means includes a micropore filter and a third needle means disposed upon one end thereof for piercing one of said vial seals and means for receiving the other end of said second needle means on the other end of said third needle means with said micropore filter being disposed therebetween for causing said mixed medicaments to pass through said micropore filter before entering said patient.

3. A wet-dry syringe according to claim 1 wherein said second needle means is removably retained by said vial lips while piercing the other of said pair of vial seals.

4. A wet-dry syringe according to claim 1 wherein one of said piston rod seals is an integral part of said piston rod means and includes said second needle means, and needle cover means for retaining said liquid medicament in said piston rod means and maintaining the sterility of said second needle means.

5. A wet-dry syringe according to claim 1 wherein said one of said piston rod seals is provided with means for removably affixing a third needle means thereto for piercing said second piston rod seal simultaneously with the piercing of said remaining vial seal and providing a communicating fluid flow path between said second medicament and said first medicament.

6. A wet-dry syringe according to claim 1 wherein said piston rod further includes resilient collapsible membrane means for containing said second liquid medicament disposed between said first and second piston rod seals.

7. A wet-dry syringe according to claim 1 wherein said piston rod means further includes a protruding lip portion disposed proximate said first piston rod seal and a removable end cap adapted to be disposed thereover and cooperate with said protruding lip portion.

8. The method of combining and mixing a liquid and a solid medicament or at least two dissimilar liquid medicaments prior to the application thereof to a patient comprises, the steps of:
    (a) providing a vial having identical end seals with a solid or liquid disposed between said seals by a vacuum process;
    (b) providing a hollow piston rod having a liquid medicament disposed therein between a fixed and a movable end seal;
    (c) providing a hollow piercing means proximate said fixed piston rod seal;
    (d) engaging one of said vial seals with said piston rod with said piercing means disposed therebetween;
    (e) applying pressure between said piston rod and said vial for said piercing means to puncture said fixed piston rod seal;
    (f) drawing said piston rod away from said vial and moving said vial seal proximate one end of said vial, said hollow piercing means providing a fluid flow path between said vial medicament and said piston rod medicament, said piston rod medicament entering said vial because of said pressure differential generated therebetween;

(g) connecting a needle assembly means having a seal piercing means on one end and a patient piercing means on the other end to said vial;

(h) puncturing said remaining vial seal with said needle assembly means; and (i) applying pressure to said piston rod in the direction of said vial to cause said combined medicament to leave said needle assembly means into said patient.

9. The method of combining and mixing a liquid and a solid medicament according to claim 8 wherein said hollow piercing means is of the dual type having piercing points at both ends and in step (e) said dual piercing means punctures said piston rod seal simultaneously with puncturing said vial seal.

* * * * *